United States Patent [19]

Kolbly

[11] Patent Number: 5,383,470
[45] Date of Patent: Jan. 24, 1995

[54] PORTABLE SPIROMETER

[75] Inventor: Kenneth Kolbly, Barstow, Calif.
[73] Assignee: Steve Novak, Burmuda Dunes, Calif.
[21] Appl. No.: 126,702
[22] Filed: Sep. 20, 1993
[51] Int. Cl.⁶ ............................................. A61B 5/087
[52] U.S. Cl. .................... 128/725; 128/726; 73/861.74; 73/861.75
[58] Field of Search ............... 128/716, 725, 726, 727; 482/13; 73/861.74, 861.75

[56] References Cited

U.S. PATENT DOCUMENTS

| | | | |
|---|---|---|---|
| 3,611,801 | 10/1971 | Fagot et al. | 73/194 A |
| 3,922,525 | 11/1975 | Kozak et al. | 128/725 |
| 3,946,726 | 3/1976 | Pikul | 73/861.74 |
| 3,955,415 | 5/1976 | Sharon | 73/861.74 |
| 4,428,242 | 1/1984 | Holstrom | 73/861.75 |
| 4,441,505 | 4/1984 | Edwards et al. | 128/726 |
| 4,945,344 | 7/1990 | Farrell et al. | 73/861.74 |
| 4,981,139 | 1/1991 | Pfohl | 128/671 |
| 4,984,158 | 1/1991 | Hillsman | 364/413.04 |
| 5,033,312 | 7/1991 | Stupecky | 128/725 |
| 5,107,846 | 4/1992 | Atlas | 128/666 |
| 5,137,026 | 8/1992 | Waterson et al. | 128/725 |
| 5,277,195 | 1/1994 | Williams | 128/725 |

FOREIGN PATENT DOCUMENTS

| | | | |
|---|---|---|---|
| 3141879 | 5/1983 | Germany | 73/861.74 |
| 3833610 | 7/1989 | Germany | 128/726 |
| 1442218 | 12/1988 | U.S.S.R. | 482/13 |

OTHER PUBLICATIONS

Respiration Transducer by C. R. Willis, IBM Technical Disclosure Bulletin, vol. 6, No. 6, Nov. 1963.

Primary Examiner—K. M. Pfaffle
Attorney, Agent, or Firm—Louis L. Dachs

[57] ABSTRACT

The invention is a portable spirometer for measuring the respiration rate of a patient. In detail, the invention includes a housing having a top and bottom, and first and second ends with an air passage extending therethrough. An air flow sensing member is movably mounted within the passage, the member movable forwards and backwards in response to the directional flow of air in the passage as the patient breaths in and out one end of the passage. A position sensing system is mounted within the housing for sensing the position of the air flow sensing member, the sensing system providing a first output signal when the air flow sensing member moves forward and backwards. A circuit is coupled to the sensing system for counting the number of times per unit time the air flow sensing member moves forward and backwards and provides a second signal proportional thereto. A display device is coupled to the circuit and receives the second output signal and displays the number of times per unit time the air flow sensing member moves forward.

6 Claims, 3 Drawing Sheets

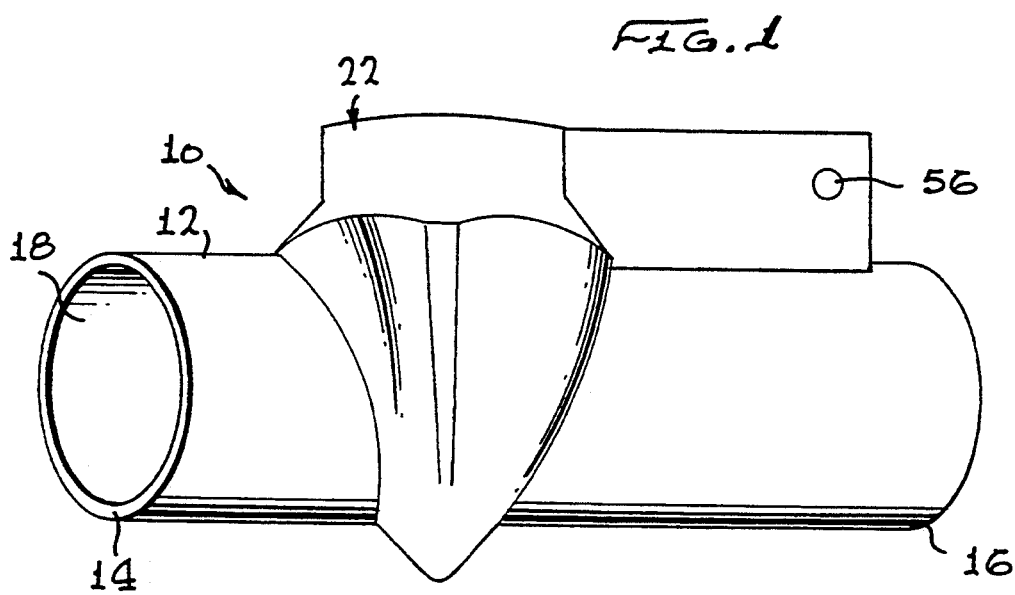
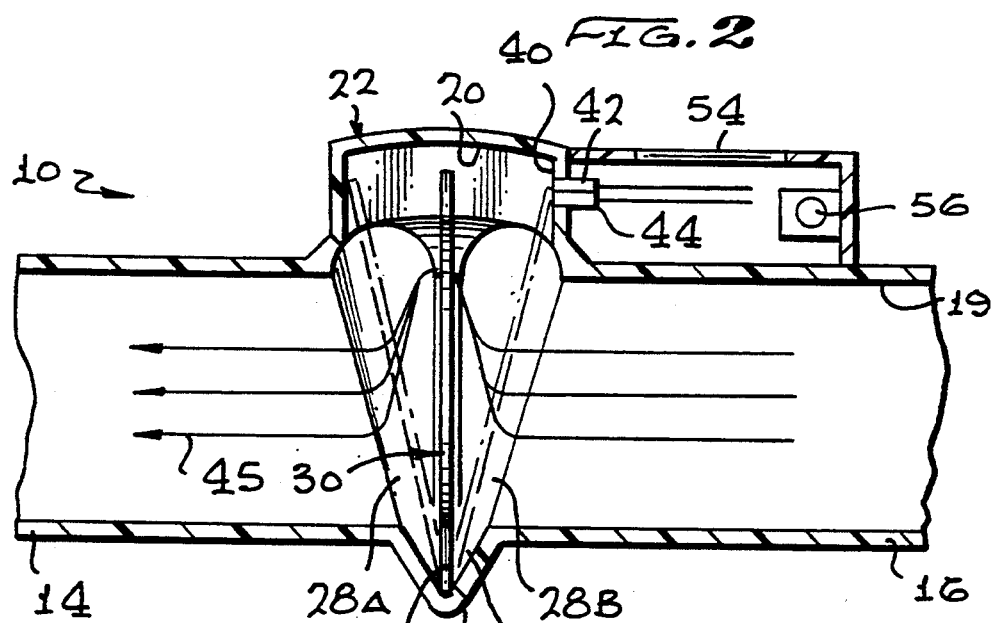
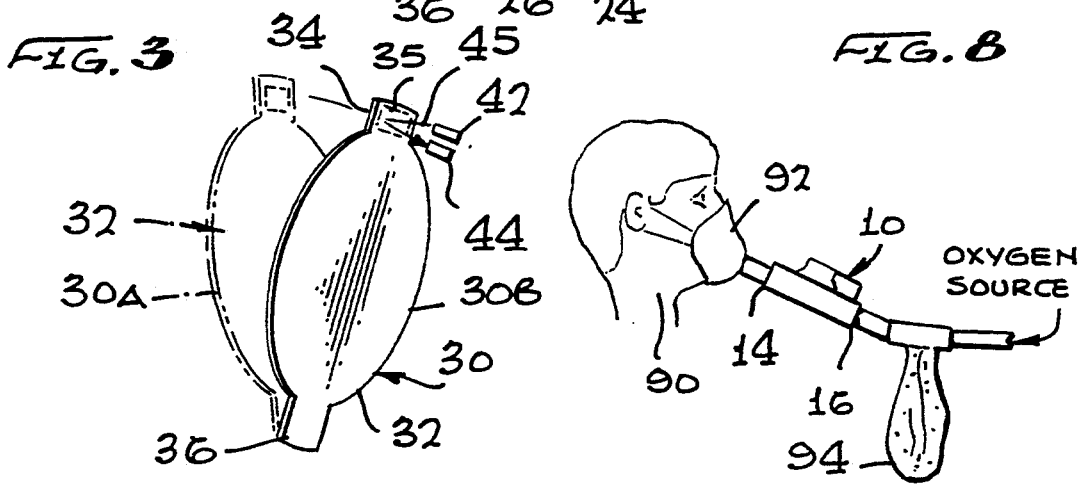

PORTABLE SPIROMETER

BACKGROUND OF THE INVENTION

1. Field of the Invention

The invention is a device for measuring the respiration rate of a patent, in particular, to a portable hand held device for making such measurements.

2. Description of Related Art

There are two major types of devices that measure the respiration rate of a patient; one type measures the expansion and contraction of the chest cavity and the other type measures the respiration by sensing the airflow into and out of the lungs during inhaling and exhaling. A description of the former type can be found in IBM Technical Disclosure Bulletin, Vol 6, No. 6, November 1963 wherein a respiration transducer by G. R. Willis is disclosed. This respiration transducer comprises a chest band having a first end attached to a housing and a second end attached to a mirror movably mounted within the housing. The Mirror is biased toward the first end of the band by a spring mounted within the housing. A lamp and light sensor are mounted within the housing, separated by a light barrier. As the patient breathes, the mirror is moved away and toward the lamp and the sensor; thus creating a series of pulses that can be counted and which correspond to the breathing rate. In U.S. Pat. No. 5,107,846, "Displacement Detector Device and Method" by D. Atlas a similar system. Here the mirror is moved back and forth across the end of a optical fiber. A LED/photodiode transmits and receives light transmitted down a optical fiber and reflected off the mirror. The interruption of the signal as the mirror is moved back and forth under the optical fiber as the patient breaths in and out providing an indication of the respiration rate. While these devices will record respiration rates, they have the disadvantage of requiring that they be attached about the patient's chest. This is a time consuming operation and, in some cases, particularly if the patient can not be moved, they can not be used at all.

In U.S. Pat. No. 4,981,139, "Vital Signs Monitoring And Communication System by R. L. Pfohl a sound sensor attached to the chest is used to monitor the respiration rate. Here the patient need not be moved to achieve attachment of the device; however, it is not a self contained unit. Additionally, as with the Willis and Atlas devices they depend on significant movement of the chest wall to produce a signal. If the respiration is shallow meaningful readings may not be obtainable. It is also difficult to differentiate body movement from respiration if the patient is in motion.

An example of the second type can be found in U.S. Pat. No. 3,611,801, Respiration Monitor" by R. J. Fagot, et al. In the Fagot, et al device the patient breaths through a tube with connects directs to a housing having a microphone mounted therein. The sound of the air rushing passed the microphone is recorded as electrical pulses that can be counted. The problem with this device is that it requires sophisticated electronic circuits such as pulse shapers and, thus is unnecessarily expensive.

In the devices disclosed in U.S. Pat. Nos. 5,137,026, "Personal Spirometer" by C. K. Waterson, et al. and 4,984,158, "Metered Dose Inhaler, Biofeedback Training And Evaluation System" by E. Hillsman the patient breaths into a tube connected to a housing having an orifice mounted therein. The respiration rate is determined by measuring the pressure drop across an orifice by a differential pressure transducer. Here again sophisticated electronic circuitry is necessary in order to eliminate spurious signals and provide accuracy.

Thus, it is a primary object of the invention to provide a portable respiration rate measuring device.

It is another primary object of the invention to provide a portable respiration rate measuring device that is inexpensive to manufacture.

It is a further object of the invention to provide a portable respiration rate measuring device that is extremely accurate.

SUMMARY OF THE INVENTION

The invention is a portable spirometer for measuring the respiration rate of a patient. In detail, the spirometer includes a housing having a top and bottom and first and second ends with an air passage extending therethrough. An air flow sensing member is movably mounted within the passage, the member movable forwards and backwards in response to the directional flow of air in the passage as the patient breaths in and out of one end. Preferably, the airflow sensing member comprises a plate having top and bottom portions. The plate is pivotally mounted by its bottom portion at the bottom of the housing and the top portion of the plate extends to the top of the housing, the plate being sufficiently smaller than the passage such that air can flow in the passage about the plate.

A position sensing system is mounted within the housing for sensing the position of the air flow sensing member. The sensing system provides a first output signal when the air flow sensing member moves forward and backwards. The sensing system preferably consists of a reflective surface on the plate; a light source mounted in the housing for directing a beam of light onto the reflective surface when the plate is proximity to the light source; and a photo detector mounted in the housing for detecting the beam of light reflected off the reflected surface when the plate is in proximity to the light source. The photo detector, which is preferably mounted in proximity to the light source, is adapted to provide a first output signal upon receipt of the reflected beam of light.

A circuit is coupled to the sensing system for counting the number of times per unit time the air flow sensing member moves forward and backwards and provides a second signal proportional thereto that is directed to a visual display for displaying the number of times per unit time the air flow sensing member moves forward and or backwards. Preferably, the circuit is a microprocessor adapted to receive the first output signal from the photo detector and provide the second output signal proportional to the number of times per unit time the plate is in the forward position. Of course, a conventional electrical circuit could be used to receive the first output signal and provide the second output signal to the display.

The novel features which are believed to be characteristic of the invention, both as to its organization and method of operation, together with further objects and advantages thereof, will be better understood from the following description in connection with the accompanying drawings in which the presently preferred embodiment of the invention is illustrated by way of example. It is to be expressly understood, however, that the drawings are for purposes of illustration and description only and are not intended as a definition of the limits of the invention.

BRIEF DESCRIPTION OF THE DRAWINGS

FIG. 1 is perspective view of the spirometer.

FIG. 2 is a cross-sectional view of the spirometer shown in FIG. 1.

FIG. 3 is a perspective view of the position sensing member shown in its forward and backward position.

FIG. 8 is a partial view of a patient using the spirometer.

DESCRIPTION OF THE PREFERRED EMBODIMENT

Figure 4A:
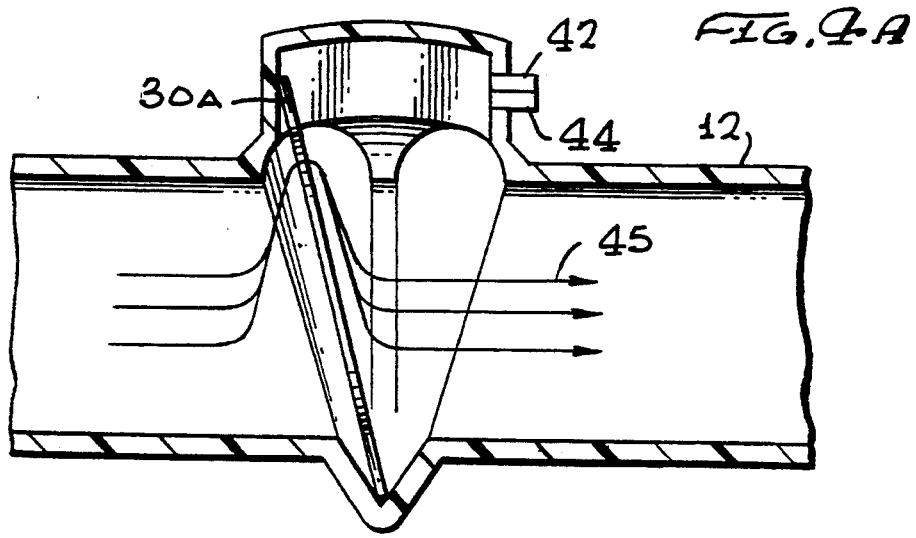
FIG. 4A is a partial view of the spirometer shown in FIG. 2 illustrating the position sensing member in the forward position.
Figure 4B:
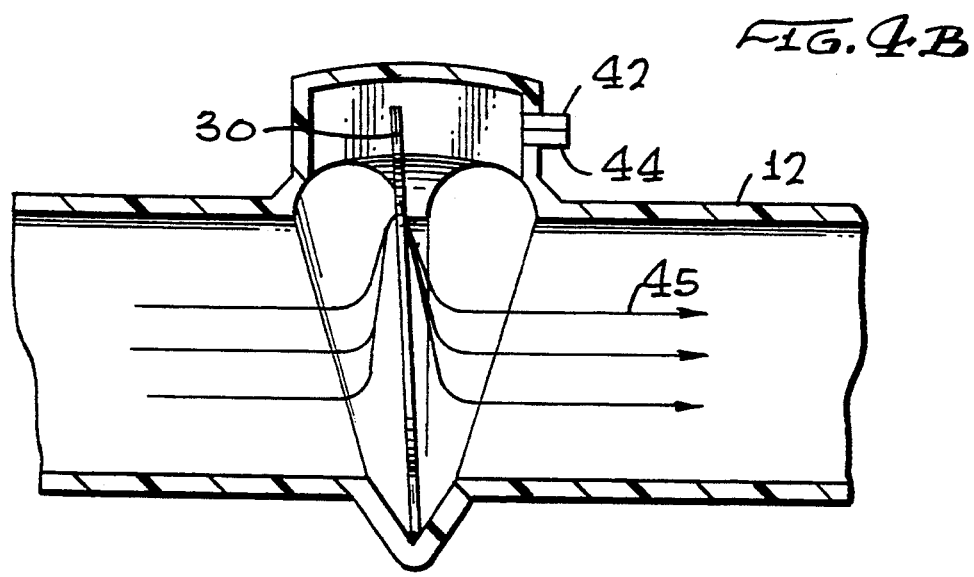
FIG. 4B is a view of the spirometer similar to FIG. 4A illustrating the position sensing member in the middle position.
Figure 4C:
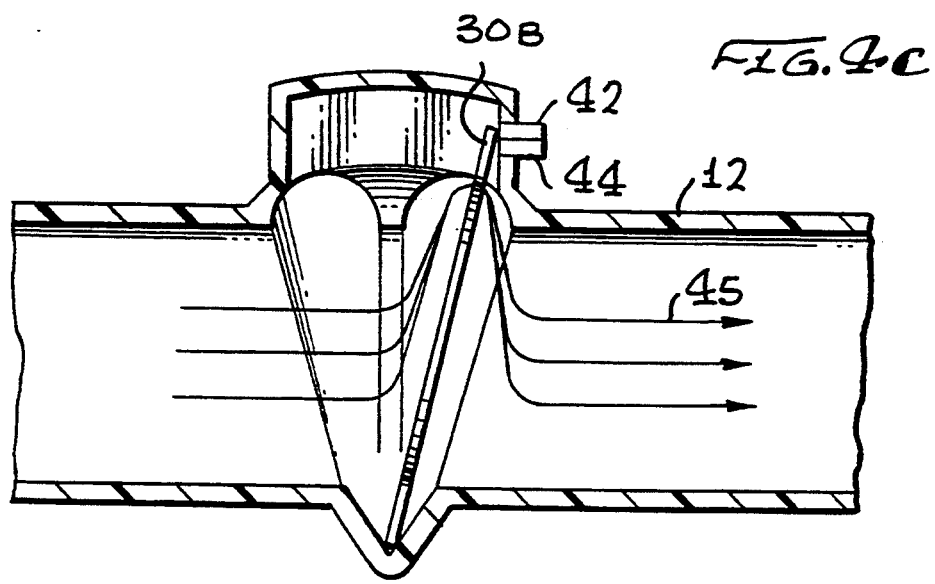
FIG. 4C is a view of the spirometer similar to FIG. 4A illustrating the position sensing member in the backward position.

Referring to FIGS. 1, 2, 3 and 4A through 4C it can be seen that the spirometer, generally indicated by numeral 10, includes a housing 12 having first and second ends, 14 and 16, respectively. A passage 18, having an inner wall 19 extends through the housing from the first end 14 to the second end 16. The passage includes an internal compartment 20 at the top 22 of the housing 10 and a "V" shaped groove 24 at the bottom 26. Two tapered slots 28A and 28B are positioned in the inner wall 19 and extend from the top 22 toward each other and meet at to the bottom 26.

An air flow sensing member in the form of a plate 30 is mounted within the passage 18 having a round portion 32, a rectangular shaped portion 34 having a reflective surface 35, that fits into the compartment 20 at the top 22 of the housing 10 and a small tap portion 36 that rides in the V shaped groove 24 at the at the bottom 26. The plate 30 is sized so that it can easily pivot forwards (position 30A) and backwards (position 30B) about the tab portion 36 riding in the groove 24 such that the rectangular shaped portion 34 moves backwards and forwards in the compartment 20. Mounted in the wall 40 of the compartment 20 is a light source in the form of a light emitting diode 42 and a photo detector 44. Thus, with the diode 42 emitting a beam of light, indicated by numeral 45, the photo detector 44 will sense the light reflected off the reflective surface 35 when the plate 30 is in the backwards position 30B. Thus as the patient breathes in and out of the first end 14 of the housing, the airflow moving backwards and forwards, causing the plate 30 to move forwards (30A) and backwards (30B). The total number of breaths will be detected by the photo detector 44.

Figure 5:
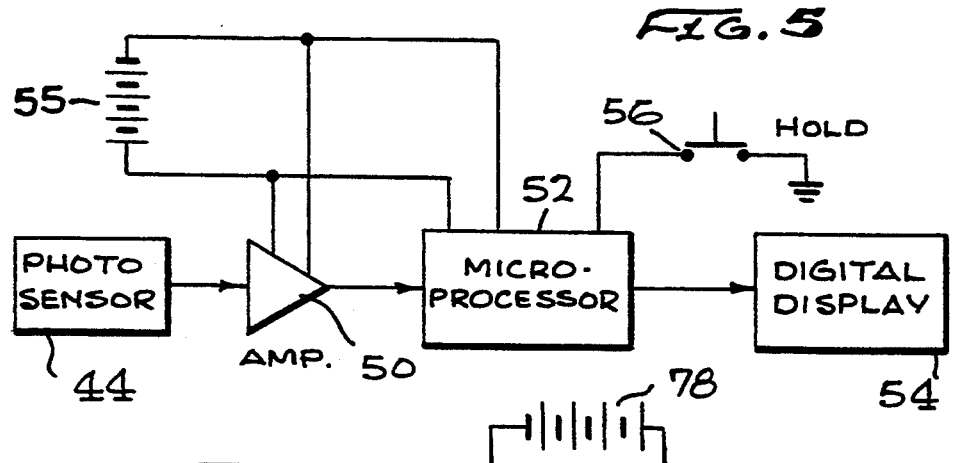
FIG. 5 is a block diagram of second embodiment of the electronic circuitry involving the use of a microprocessor.

Referring to FIG. 5 the photo detector 44 is coupled to an amplifier 50 and provides a first output signal thereto that is proportional to the number of times the plate 30 moves to the backwards position (one breathing cycle) the output from the amplifier 50 is fed to a micro-possessor 52 wherein the number of times per minute (or any unit of time) the plate 30 moves backwards (position 30B). Again this is directly proportional to the respiration rate of the patient. A second output signal from the micro-processor 52 is fed to a visual display unit 54 wherein the respiration rate can be read. A hold switch 56 is coupled to the micro-processor 52 for causing it to hold a reading in the visual display 54. A battery 55 is coupled to the amplifier 50 and microprocessor 52 providing power thereto.

Figure 6:
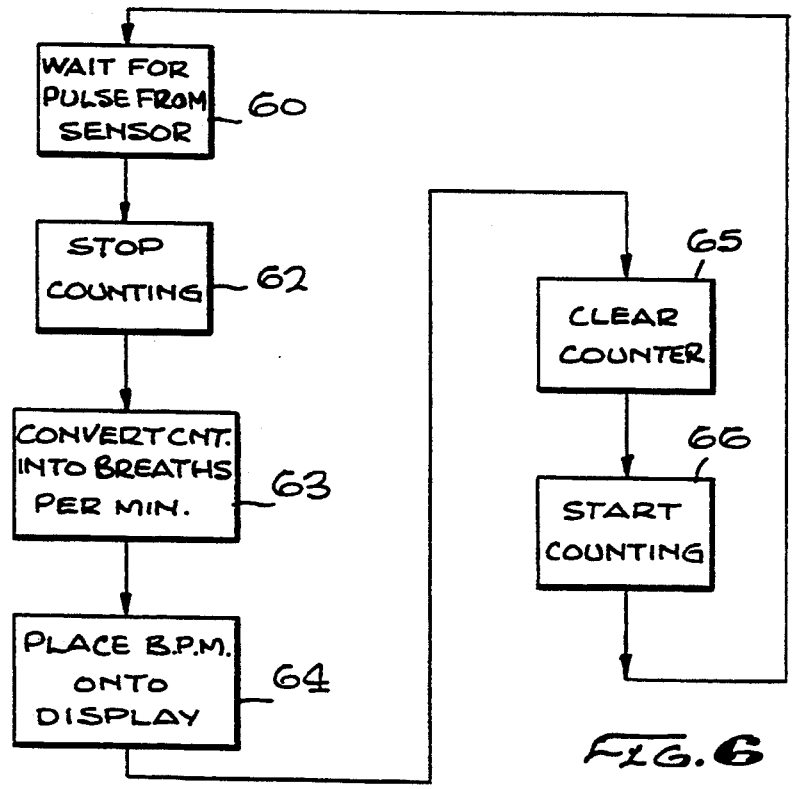
FIG. 6 is a block diagram of a computer program suitable for use in the micro-processor shown in FIG. 5.

The programming of the micro-processor 52 is a simple matter and a six step flow chart of a computer program is shown in FIG. 6:

1. Wait for pulse from sensor (60); the microprocessor will wait at this point until the first signal is received from the sensor 44.
2. Stop counting (62); the microprocessor will stop the internal timer.
3. Convert count to breaths per minute (63); by means of a math operation or table look-up the number from the internal timer into a number that represents the actual number of breaths-per-minute.
4. Place breaths per minute (BPM) onto display (64); the above number from step 3 so that the display 54 can present the BPM to the operator in a visual form
5. Clear counter (65); reset the internal timer to zero again
6. Start counting (66); start the internal timer counting again. Such computer programs are simple to accomplish, requiring little, effort by those skilled in the art of computer programming.

Figure 7:
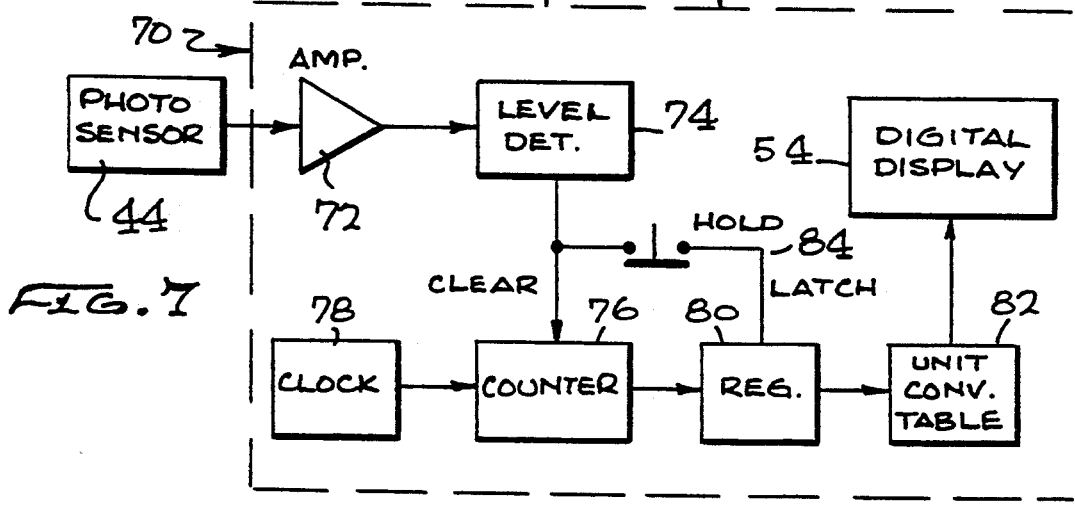
FIG. 7 is a block diagram of a first embodiment of the electronic circuitry.

In FIG. 7 is an electronic circuit, generally indicated by numeral 70, is illustrated which can perform the same calculation of the respiration rate. In this circuit, the output from the photo detector is coupled to a amplifier 72. The output from the amplifier 72 is coupled to a level detector 74 that prevents a spurious signal from being counted as a breath. The output from the level detector 74 is coupled to a counter 76 that also receives a signal from a clock 78. The output from the counter 76 in turn is fed to a register 80, to a unit conversion table circuit 82 and finally to the display 54. A latch 84 is coupled to both the counter 76 and register 80 to provide for both holding a "displayed respiration rate" and for clearing the counter 76. A battery 78 is coupled to the circuit for providing electrical power thereto. Here again, the circuit 70 is a simple one easily assembled by one with ordinary skill in the electronic arts and, therefore, need not be discussed in further detail.

In FIG. 8, a patient 90 is shown wearing an oxygen mask 92. The spirometer 10 is coupled by its first end 14 directly to the mask 92, while the second end 16 is coupled to a breathing bag 94, that, in turn, is coupled to a source of oxygen (not shown). Thus while the patient breaths, his respiration rate is automatically measured. Because the plate 30 is unrestrained, even tiny infants, whose breath is weak, can be effectively monitored.

While the invention has been described with reference to a particular embodiment, it should be understood that the embodiment is merely illustrative as there are numerous variations and modifications which may be made by those skilled in the art. Thus, the invention is to be construed as being limited only by the spirit and scope of the appended claims.

INDUSTRIAL APPLICABILITY

The invention relates to the medical industry and industries supplying medical monitoring devices.

I claim:

1. A portable spirometer for measuring a respiration rate of a patient comprising:
    a housing having a top and bottom and first and second ends, said housing having an air passage extending therethrough said first and second ends;
    an air flow sensing plate having top and bottom portions movably mounted within said passage, said plate pivotally mounted by said bottom portion at said bottom of said housing and said top portion of said plate extending to said top of said housing, said plate movable forwards and backwards in response to the directional flow of air in said passage as the patient breaths in and out said first end, said plate sufficiently smaller than said passage such that air can flow in said passage about said plate;
    position sensing means mounted within said housing for sensing the position of said air flow sensing plate, said position sensing means providing a first output signal when said air flow sensing plate moves forward and backwards;
    circuit means coupled to said sensing means for counting the number of times per unit time said air flow sensing plate moves forward and backwards and providing a second signal proportional to the respiration rate; and
    display means coupled to said circuit means and receiving said second output signal for displaying the respiration rate.

2. The spirometer as set forth in claim 1 wherein said position sensing means comprises:
    said plate having a reflective surface;
    a light source mounted in said housing for directing a beam of light onto said reflective surface when said plate is in proximity to said light source; and
    a photo detector mounted in said housing for detecting the beam of light reflected off said reflective surface when said plate is in proximity to said light source, said photo detector providing said first output signal upon receipt of the reflected beam of light.

3. The spirometer as set forth in claim 2 wherein said reflective surface is located in proximity to said top portion of said plate.

4. The spirometer as set forth in claim 3 wherein said light source and said photo detector are in proximity to each other.

5. The spirometer as set forth in claim 4 further including power supply means disposed in said housing for supplying electrical power to said light source, said photo detector, said circuit means and said display means.

6. The spirometer as set forth in claim 2, or 3, or 4, or 5 wherein said circuit means comprises a microprocessor means for receiving said first output signal from said photo detector and for providing said second output signal to said display means.

* * * * *